US007859170B2

(12) United States Patent
Knowles et al.

(10) Patent No.: US 7,859,170 B2
(45) Date of Patent: Dec. 28, 2010

(54) WIDE-BANDWIDTH MATRIX TRANSDUCER WITH POLYETHYLENE THIRD MATCHING LAYER

(75) Inventors: Heather Knowles, Devens, MA (US); Jacquelyn Byron, Windham, NH (US)

(73) Assignee: Koninklijke Philips Electronics N.V., Eindhoven (NL)

( * ) Notice: Subject to any disclaimer, the term of this patent is extended or adjusted under 35 U.S.C. 154(b) by 791 days.

(21) Appl. No.: 11/771,187

(22) Filed: Jun. 29, 2007

(65) Prior Publication Data

US 2009/0000383 A1 Jan. 1, 2009

Related U.S. Application Data

(63) Continuation-in-part of application No. 12/063,294, filed as application No. PCT/IB2006/052476 on Jul. 19, 2006.

(60) Provisional application No. 60/706,399, filed on Aug. 8, 2005.

(51) Int. Cl.
*H01L 41/09* (2006.01)
*A61B 8/00* (2006.01)
*G01N 29/28* (2006.01)

(52) U.S. Cl. .................................................... 310/334

(58) Field of Classification Search ................. 310/334
See application file for complete search history.

(56) References Cited

U.S. PATENT DOCUMENTS

| | | | | | |
|---|---|---|---|---|---|
| 2,949,910 | A * | 8/1960 | Brown et al. | ................ | 600/528 |
| 4,166,967 | A * | 9/1979 | Benes et al. | ................ | 310/338 |
| 6,396,199 | B1 * | 5/2002 | Douglas et al. | ............. | 310/335 |
| 6,666,825 | B2 * | 12/2003 | Smith et al. | ................. | 600/459 |
| 2002/0000763 | A1 * | 1/2002 | Jones | ......................... | 310/337 |
| 2007/0108872 | A1 * | 5/2007 | Shibamoto et al. | .......... | 310/322 |

FOREIGN PATENT DOCUMENTS

| | | | | |
|---|---|---|---|---|
| JP | 2004-120283 | A | * | 4/2005 |
| JP | EP-1542005 | A1 | * | 6/2005 |
| JP | 2007-288396 | A | * | 11/2007 |
| JP | 2007-288397 | A | * | 11/2007 |

* cited by examiner

*Primary Examiner*—Thomas M Dougherty
(74) *Attorney, Agent, or Firm*—W. Brinton Yorks, Jr.

(57) ABSTRACT

A third matching layer (140) affording wide bandwidth for an ultrasound matrix probe is made of polyethylene, and may extend downwardly to surround the array (S360) and attach to the housing to seal the array (S370).

16 Claims, 4 Drawing Sheets

WIDE-BANDWIDTH MATRIX TRANSDUCER WITH POLYETHYLENE THIRD MATCHING LAYER

This application is a continuation-in-part of U.S. patent application Ser. No. 12/063,294, yet to be filed, which U.S. Patent Application stems from PCT Application No. IB2006/052476 (Pub. No. WO2007/017776A2), filed Jul. 19, 2006, which PCT Application in turn stems from U.S. Provisional Patent Application Ser. No. 60/706,399, filed Aug. 8, 2005.

An ultrasound transducer serves to convert electrical signals into ultrasonic energy and to convert ultrasonic energy back into electrical signals. The ultrasonic energy may be used, for example, to interrogate a body of interest and the echoes received from the body by the transducer may be used to obtain diagnostic information. One particular application is in medical imaging wherein the echoes are used to form two and three dimensional images of the internal organs of a patient. Ultrasound transducers use a matching layer or a series of matching layers to more effectively couple the acoustic energy produced in the piezoelectric to the body of the subject or patient. The matching layers lie above the transducer, in proximity of the body being probed. Acoustic coupling is accomplished, layer-by-layer, in a manner analogous to the functioning of respective anti-reflection coatings for lenses in an optical path. The relatively high acoustic impedance of the piezoelectric material in a transducer in comparison to that of the body is spanned by the intervening impedances of the matching layers. A design might, for example, call for a first matching layer of particular impedance. The first matching layer is the first layer encountered by the sound path from the transducer to the body. Each successive matching layer, if any, requires progressively lower impedance. The impedance of the topmost layer is still higher than that of the body, but the one or more layers provide a smoother transition, impedance-wise, in acoustically coupling the ultrasound generated by the piezoelectric to the body and in coupling the ultrasound returning from the body to the piezoelectric.

Optimal layering involves a design of an appropriate series of acoustic impedances and the identification of respective materials. Materials used in the matching layers of one-dimensional (1D) transducers whose elements are aligned in a single row include ceramics, graphite composites, polyurethane, etc.

Although 1D transducers have been known to include a number of matching layers, transducers configured with a two-dimensional (2D) array of transducer elements require a different matching layer scheme due to the different shape of the transducer elements. A traveling sound wave oscillates at a frequency characteristic of that particular sound wave, and the frequency has an associated wavelength. The elements of 1D array transducers are typically less than half a wavelength wide of the operating frequency in one transverse direction, but several wavelengths long in the other transverse direction. Elements of a 2D array transducer may be less than half a wavelength wide in both transverse directions. This change of shape reduces the effective longitudinal stiffness, and therefore, the mechanical impedance of the element. Since the element impedance is lower, it follows that the impedances of the matching layers also should be lower to achieve the best performance. A complicating factor of low impedance materials, however, is that when cut into narrow posts as in a 2D array transducer, the speed of sound becomes dependent on the frequency of the signal, a phenomenon known as velocity dispersion. This dispersion changes the matching properties of the layer with frequency, which is undesirable, and can create a cutoff frequency above which it is not possible to operate the transducer. 2D array transducers are currently built with only two matching layers, due to the lack of suitable materials for a three matching layer design. However, this limits the bandwidth and sensitivity, both of which are critical to improving performance in Doppler, color flow, and harmonic imaging modes. In the case of harmonic imaging, for example, a low fundamental frequency is transmitted to provide deeper penetration into the body tissue of the ultrasound subject or patient, but higher resolution is obtained by receiving harmonic frequencies above the fundamental. A bandwidth large enough to include diverse frequencies is therefore often desirable.

The piezoelectric elements of 1D and 2D array transducers typically have been made of polycrystalline ceramic materials, one of the most common being lead zirconate titanate (PZT). Single-crystal piezoelectric materials are becoming available, e.g., mono-crystalline lead manganese niobate/lead titanate (PMN/PT) alloys. Piezoelectric transducer elements made from these monocrystalline materials, exhibit significantly higher electromechanical coupling which potentially affords improved sensitivity and bandwidth.

The present inventors observe that the increased electromechanical coupling of single-crystal piezoelectrics also produces a lower effective acoustic impedance. As a result, it is preferable to select matching layers of acoustic impedance lower than those for a typical poly-crystalline transducer such as a ceramic one.

Since the three matching layer, mono-crystalline transducer requires matching layers with lower acoustic impedances, and since the second matching layer of an ultrasound probe transducer is always of lower impedance than its first matching layer, it is possible that a second matching layer usable for ceramic transducers, such as graphite composite, may serve as a first matching layer for a three matching layer, mono-crystalline transducer.

The first and second matching layers typically are stiff enough that the layers for each element of the array must be separated from each other mechanically to keep each element acoustically independent of the others. Most often, this is done by means of saw cuts in two directions that penetrate the two matching layers and the piezoelectric material.

Another consideration may be electrical conductivity, which would not present a problem for isotropically conductive graphite composite.

Finding a suitable second matching layer, however, may involve selecting a material with not only the proper acoustic impedance, but appropriate electrical conductivity.

A piezoelectric transducer of an ultrasound probe relies upon electric fields produced in the piezoelectric. These fields are produced and detected by means of electrodes attached to at least two faces of the piezoelectric To generate ultrasound, for example, a voltage is applied between the electrodes requiring electrical connections to be made to the electrodes. Each element of the transducer might receive a different electrical input. Terminals to the transducer elements are sometimes attached perpendicularly to the sound path, although this can be problematic for internal elements of two-dimensional matrix arrays. Accordingly, it may be preferable to attach the elements to a common ground on top of, or under, the array. A matching layer may serve as a ground plane, or a separate ground plane may be provided. The ground plane may be implemented with an electrically-conductive foil thin enough to avoid perturbing the ultrasound.

However, unless the separate ground plane is disposed between the first matching layer and the piezoelectric element, the first matching layer is preferably made electrically-conductive in the sound path direction in order to complete an electrical circuit that flows from behind and through the array. Because the 2D array elements are mechanically separated, e.g. by saw cuts in two directions producing individual posts, there is no electrical path for an element in the interior of the array laterally to the edge of the array. Accordingly, the electrical path must be completed through the matching layer. The same principle holds for the second matching layer.

Polyurethane, with an acoustic impedance of around 2.1 MegaRayls (MRayls), might serve as a third matching layer, which requires the lower impedance than the first or second layers. However, besides having an impedance somewhat higher than that desired, polyurethane is very susceptible to chemical reaction. Accordingly, polyurethane requires a protective coating to seal the polyurethane and the rest of the transducer array from environmental contamination as from chemical disinfecting agents and humidity. Moreover, from a process control perspective, different production runs may yield different thicknesses of the protective coating, leading to uneven acoustic performance among produced probes. Finally, the need for a separate process to apply the protective coating increases production cost enormously.

To overcome the above-noted shortcomings, an ultrasound transducer, in one aspect, includes a piezoelectric element, and first through third matching layers, the third layer comprising low-density polyethylene (LDPE).

In another aspect, an ultrasound transducer has an array of transducer elements arranged in a two-dimensional configuration and at least three matching layers.

Details of the novel ultrasound probe are set forth below with the aid of the following drawings, wherein.

Figure 1:
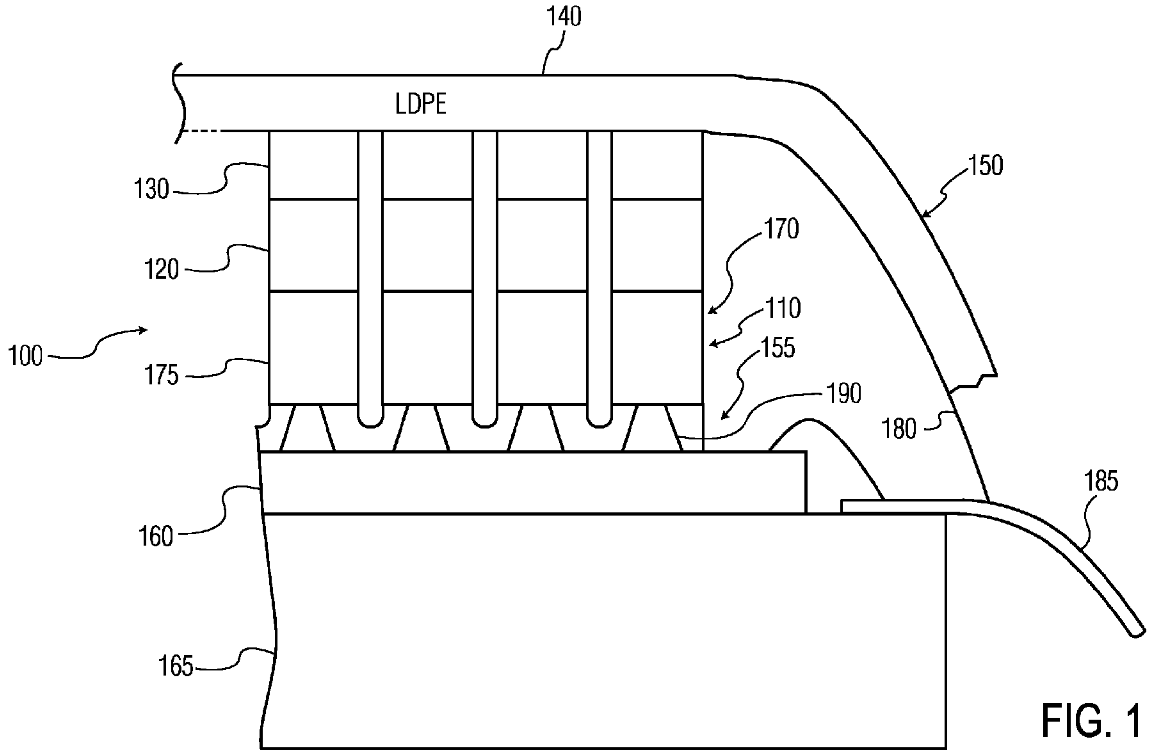
FIG. 1 is a side cross-sectional view of a matrix transducer having three matching layers, according to an illustrative aspect of the present disclosure.

FIG. 1 shows, by way of illustrative and non-limitative example, a matrix transducer 100 usable in an ultrasound probe according to the present disclosure. The matrix transducer 100 has a piezoelectric layer 110, three matching layers 120, 130, 140, a film 150 that incorporates the third matching layer 140, an interconnect layer 155, one or more semiconductor chips (ICs) 160 and a backing 165. The piezoelectric layer 110 is comprised of a two-dimensional array 170 of transducer elements 175, rows being parallel to, and columns of the array being perpendicular to the drawing sheet for FIG. 1. The transducer 100 further includes a common ground plane 180 between the second and third matching layers 130, 140 that extends peripherally to wrap around downwardly for attachment to a flexible circuit 185, thereby completing circuits for individual transducer elements 175. Specifically, the transducer element 175 is joined to a semiconductor chip 160 by stud bumps 190 or other means, and the chip is connected to the flexible circuit 185. A coaxial cable (not shown) coming from the back of the ultrasound probe typically is joined to the flexible circuit 185. The matrix transducer 100 may be utilized for transmitting ultrasound and/or receiving ultrasound.

The first matching layer 120, as mentioned above, may be implemented as a graphite composite.

Epoxy matching layers transmit sound with sufficient speed, and have density, and therefore acoustic impedance, that is sufficiently low for implementation as a second matching layer of a three-layer matrix transducer; however, epoxy layers are electrically non-conductive.

The second matching layer 130 may, for example, be a polymer loaded with electrically-conductive particles.

The third matching layer 140 is preferably made of low-density polyethylene (LDPE) and is part of the LDPE film 150 that extends downwardly in a manner similar to that of the common ground plane 180.

Figure 2:
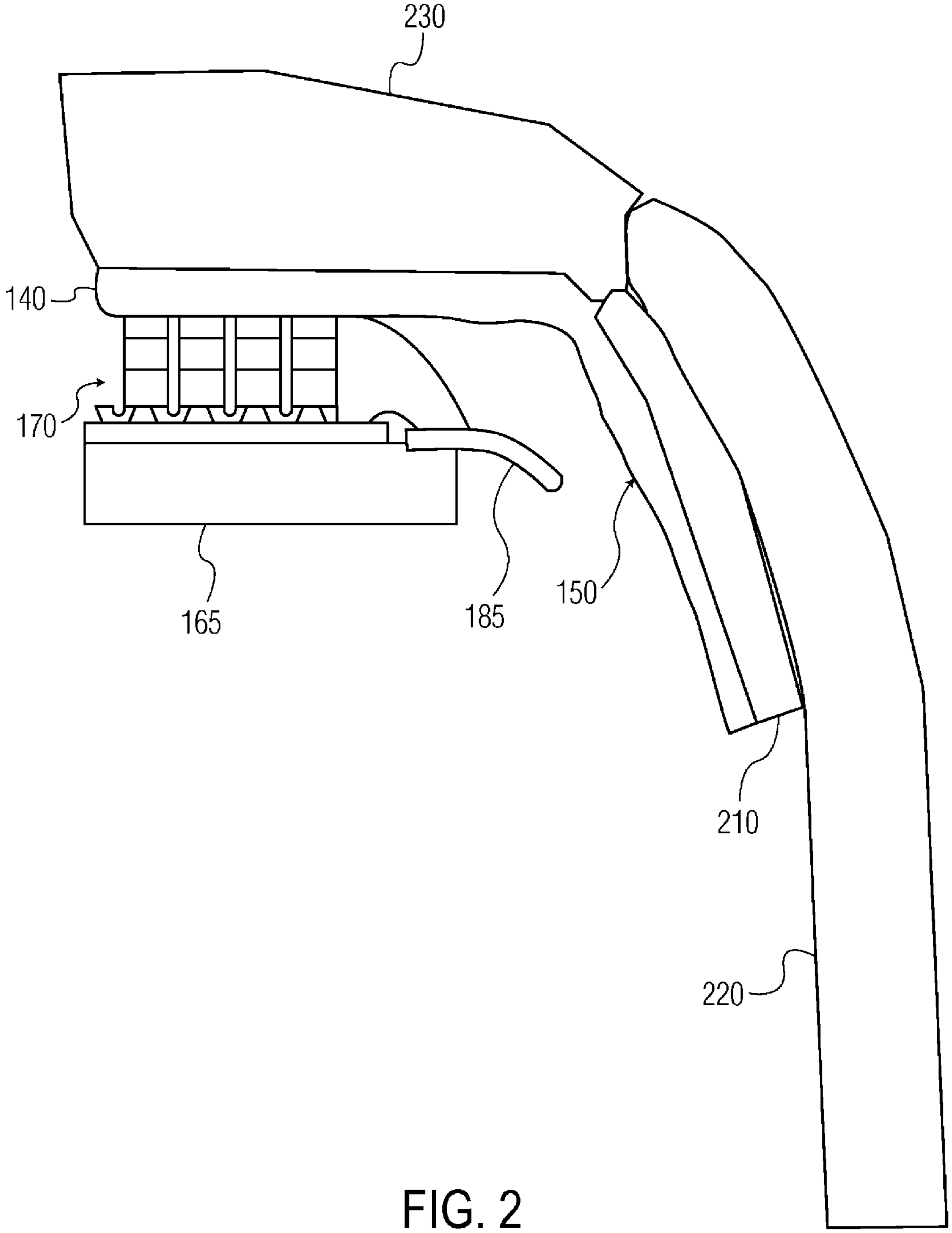
FIG. 2 is a side cross-sectional view of an example of how the third matching layer may be bonded to a transducer according to an illustrative aspect of the present disclosure.

As seen in FIG. 2, however, instead of attaching to the flexible circuit 185, the third matching layer 140 in the aspect of the present disclosure shown in FIG. 1 attaches, by way of an epoxy bond 210, to a housing 220 of the transducer 100 to form a hermetic seal around the array 170. The epoxy bond 210 also may be used between the transducer housing 220 and an acoustic lens 230 overriding the third matching layer 140.

Figure 3:
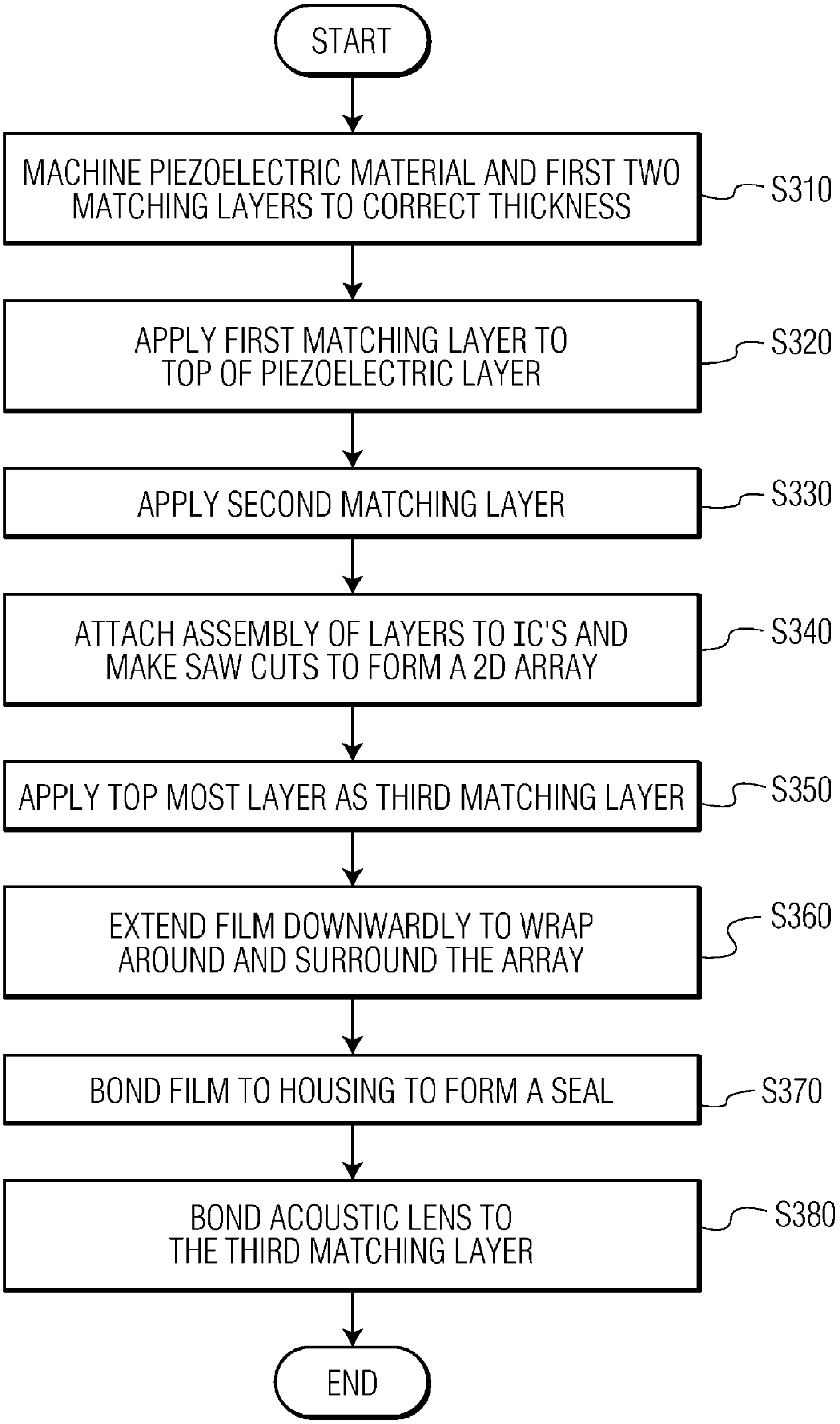
FIG. 3 is a flow chart of one example of a process according to an illustrative aspect of the present disclosure for making the transducer of FIG. 1.

FIG. 3 sets forth an illustrative process for making the probe 100 of FIG. 1 so as to include LDPE film 110 embodying the third matching layer 140. To construct the array 170, piezoelectric material and the first two matching layers 120, 130 are machined to the correct thicknesses and electrodes are applied to the piezoelectric layer 110 (step S310). After the first matching layer 120 is applied on top of the piezoelectric layer 110 (step S320), the second matching layer is applied (step S330). This assembly of layers 110, 120, 130 may be attached directly to the integrated circuits 160, if present, or to intermediary connecting means, e.g. the flexible circuit 185 or a backing structure with embedded conductors. The transducer 100 then is separated into a 2D array 170 of individual elements 175 by making multiple saw cuts in two orthogonal directions (step S340). Following the sawing operation, the ground plane 180 is bonded to the top of the second matching layer 130 and wrapped down around the array 170 to make contact with the flexible circuit 185 or other connecting means. The LDPE film 110 is applied on top and wrapped around to extend downwardly thereby surrounding the array 170. Part of the film 150 accordingly forms the topmost matching layer, which here is the third matching layer 140 (steps S350, S360). To form a hermetic seal around the array 170, the downwardly extended film 150 is bonded, as by epoxy 210, to the housing 220 (step S370). Thus, the LDPE also serves as a barrier layer. An additional step bonds the acoustic lens 230, typically a room temperature vulcanization (RTV) silicone rubber, to the third matching layer 140 (step S380). As compared to polyurethane, use of polyethylene as the third matching layer 140 eliminates the need for a protective coating, thereby cutting production cost dramatically.

Although a particular order of the steps in FIG. 3 is shown, the intended scope of the disclosure is not limited to this order. Thus, for example, the first and second matching layers 120, 130 may be bonded together before being applied as a unit to the piezoelectric material 110. Additionally, the acoustic design may call for one or more acoustic layers behind the piezoelectric layer 110.

In an alternative aspect of the present disclosure, the acoustic lens 230 is replaced with a window, i.e., an element with no focusing acoustical power. The window may be made of the window material PEBAX® (Polyether block Amide), for instance. Normally, a PEBAX window would need not only a protective layer for the polyurethane third matching layer, but, in addition, an intervening bonding layer made, for example of a polyester material such as Mylar, to bond the protective layer to the PEBAX. However, LDPE can bond directly to the PEBAX; accordingly, neither a protective layer nor a bonding layer is needed. The double layer of PEBAX window material and LDPE film 150, which may be either cut or wrapped to meet size constraints, can be made before attaching it to the second matching layer 130 connected to the array 170 by the first matching layer 120. The resulting transducer 100 with PEBAX window is usable not only for trans-esophageal echocardiography (TEE), but for other applications such as an intra-cardiac-echocardiography (ICE).

Figure 4:
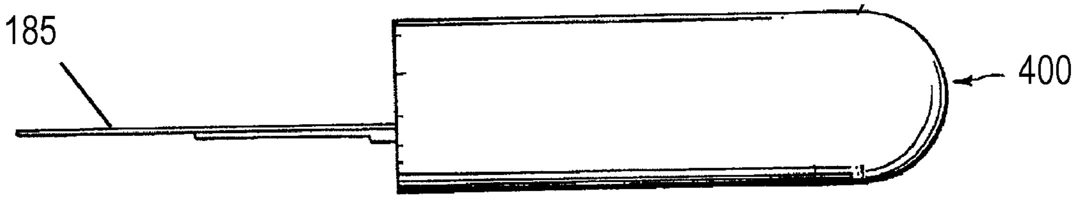
FIG. 4 is an example ultrasound catheter probe tip according to another illustrative aspect of the present disclosure.
Figure 5:
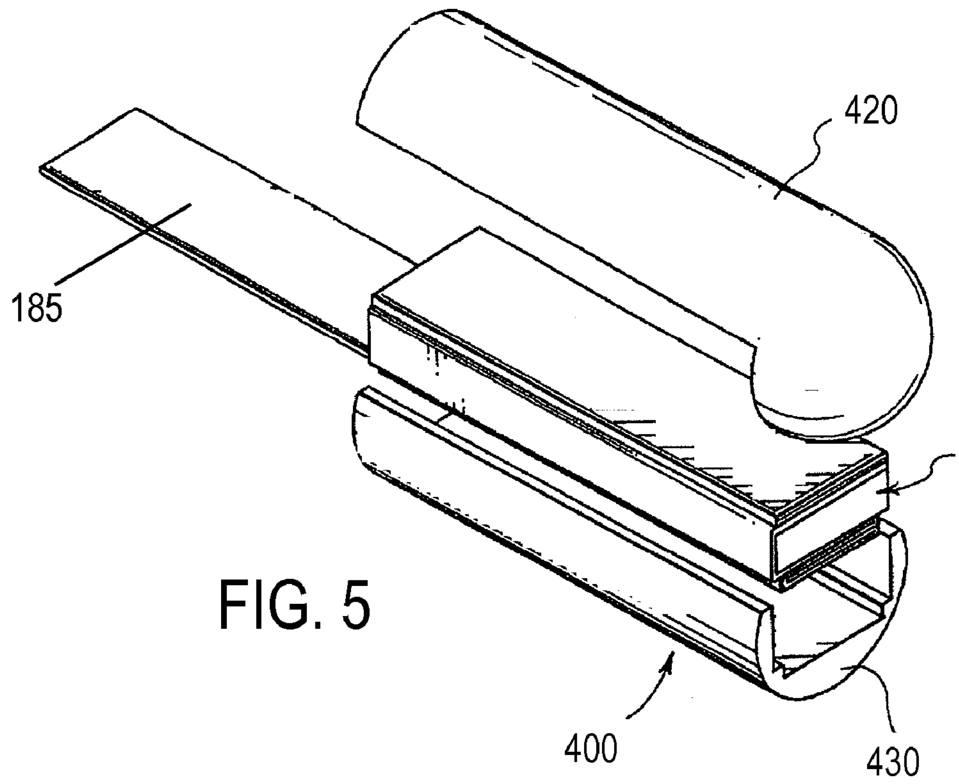
FIG. 5 is an exploded view of the probe tip of FIG. 4.

With reference to FIGS. 4 and 5, there is shown, in accordance with an illustrative aspect of the present disclosure, a catheter or probe tip 400. As shown, the tip 400 may have one or more transducers 410 preferably operatively associated with at least three matching layers such as, for example, those herein previously discussed and illustratively shown. In this aspect of the present disclosure, as PEBAX has been used for catheters, including ultrasound catheters (see, e.g., U.S. Pat. No. 6,589,182 B1), for some time due to, inter alia, the material having good biocompatibility, being easily processed for manufacturing, being available in many durometers, and being capable of bonding to itself exceptionally well (with, e.g., adhesives and/or thermal welding), and/or qualifying for use in re-usable devices/applications, the tip 400 may be made or formed partially of, and more preferably entirely of PEBAX so as to create, for example, an integrated, easy/economical to manufacture probe 100. Such a probe 100 would preferably allow for a smaller tip (e.g., by at least or about a 50% reduction of excess material), improved ergonomics, easier intubation, and improved tip contact to thereby enhance image output quality.

In another illustrative aspect of the present disclosure, the tip 400 can have two or more distinct parts 420, 430, each part preferably having distinct characteristics. For example, one part 420 can be a window portion and another part (430) can be a main body portion. In a further aspect, one part 420 can be made of one material and another part 430 can be made of either the same (with the same or differing properties) or different material. For example, the thickness and/or durometer of PEBAX used relative to, e.g., a main body portion and/or window portion may be tailored to an ideal stiffness (as opposed to, e.g., a hard plastic shell that is rigid and inflexible) for, among other things, intubation with less discomfort for a patient.

Thus, according to an advantageous aspect of the present disclosure, a relatively small two part combined tip and sensor window construction may be formed so as to eliminate many conventional manufacturing steps and thereby notably decrease cost and cycle time as the window portion may be bonded to one or more transducer elements via, e.g., a conventional thin line bond process and as the main body portion can be adhesively and/or thermally bonded to the window portion to form an integral tip that (i) can be grounded or parylene coated as needed for additional electrical isolation, (ii) may allow for better ergonomics, and (iii) may allow for more repeatable, consistent patient contact (i.e., improved image quality) as less material is required around the window.

With reference to FIGS. 1, 4 and 5, according to yet another illustrative aspect of the present disclosure, the probe 100 can be a three matching layer probe with a LDPE matching layer enabling a wide bandwidth transducer and forming at least part, and preferably all of a cover to the tip 400 and/or the probe 100 with at least one portion having appropriate thickness to form an acoustic section. In a beneficial aspect of the disclosure, the tip 400 may be operatively associated with one or more transducer elements 410, such as by being fit (sized, shaped, cut, and/or formed) over an array, and bonded to a ground plane and joined to the probe 100. In addition, or alternatively, PEBAX may form a portion of the tip 400 as appropriate to take advantage of the benefits provided thereby without compromising other beneficial features associated with an LDPE tip (e.g., the acoustic pathway).

In view of the foregoing, it is perhaps significant to note that the illustrative aspects, features and arrangements discussed herein advantageously at least allow for an extremely robust design (e.g., conforming to industry standards such as EN10555: Sterile, single use intra-vascular catheters), as well as of course blood contact biocompatibility.

The inventive matching layers may be incorporated into other types of probes such as pediatric probes, and onto various types of arrays such as curved linear and vascular arrays.

Although above aspects and features of the present disclosures are described with three matching layers, additional matching layers may intervene, as between the second and topmost matching layers 130, 140.

While there have shown and described and pointed out fundamental novel features of the present disclosure as applied to preferred aspects and features thereof, it will be understood that various omissions and substitutions and changes in the form and details of the devices illustrated, and in their operation, may be made by those skilled in the art without departing from the spirit of the present disclosure. For example, it is expressly intended that all combinations of those elements and/or method steps which perform substantially the same function in substantially the same way to achieve the same results are within the scope of the present disclosure. Moreover, it should be recognized that structures and/or elements and/or method steps shown and/or described in connection with any disclosed form or aspect of the present disclosure may be incorporated in any other disclosed or described or suggested form or aspects or features as a general matter of design choice. It is the intention, therefore, to be limited only as indicated by the scope of the claims appended hereto.

The invention claimed is:

1. An ultrasound probe comprising:

a tip having at least one transducer and at least three matching layers, a first matching layer with a first impedance, a second matching layer with a second impedance that is less than the first impedance, and a third matching layer with a third impedance that is less than the second impedance, wherein the third matching layer forms at least part of a cover to the probe, wherein the tip has a first body portion with first characteristics and a second body portion with second characteristics, wherein the first and second characteristics are material characteristics of LDPE.

2. The probe of claim 1, wherein the third matching layer is either low-density polyethylene (LDPE) or PEBAX, or some combination of both.

3. The probe of claim 1, wherein the first and second body portions are bonded together.

4. The probe of claim 1, wherein the first and second body portions are cohesively formed.

5. An ultrasound probe comprising:

a tip having at least one transducer and at least three matching layers, a first matching layer with a first impedance, a second matching layer with a second impedance that is less than the first impedance, and a third matching layer with a third impedance that is less than the second impedance, wherein the third matching layer forms at least part of a cover to the probe, wherein the tip has a first body portion with first characteristics and a second body portion with second characteristics, wherein the first and second characteristics are material characteristics of PEBAX.

6. An ultrasound probe comprising:

a tip having at least one transducer and at least three matching layers, a first matching layer with a first impedance, a second matching layer with a second impedance that is less than the first impedance, and a third matching layer with a third impedance that is less than the second impedance, wherein the third matching layer forms at least part of a cover to the probe, wherein the tip has a first body portion with first characteristics and a second body portion with second characteristics, wherein the first characteristics are material characteristics of LDPE and the second characteristics are material characteristics of PEBAX.

7. An ultrasound probe comprising:

a tip having at least one transducer and at least three matching layers, a first matching layer with a first impedance, a second matching layer with a second impedance that is less than the first impedance, and a third matching layer with a third impedance that is less than the second impedance, wherein the third matching layer forms at least part of a cover to the probe, wherein the tip has a first body portion with first characteristics and a second body portion with second characteristics, wherein the first body portion forms a window and the second body portion forms a main body of the tip.

8. A tip for an ultrasound probe, the tip comprising:

at least one transducer;

at least three matching layers;

a first body portion having first characteristics; and a second body portion having second characteristics, wherein the first and second characteristics are material characteristics of low-density polyethylene (LDPE).

9. The tip of claim 8, wherein the first and second characteristics are material characteristics of PEBAX.

10. The tip of claim 8, wherein each of the three matching layers has distinct impedance.

11. The tip of claim 10, wherein a first of the three matching layers has a first impedance, a second of the three matching layers has a second impedance that is less than the first impedance, and a third of the three matching layers has a third impedance that is less than the second impedance.

12. A tip for an ultrasound probe, the tip comprising:

at least one transducer;

at least three matching layers;

a first body portion having first characteristics; and a second body portion having second characteristics, wherein the first characteristics are material characteristics of LDPE and the second characteristics are material characteristics of PEBAX.

13. A method of making a probe tip comprising:

providing one or more transducer elements; and providing the one or more transducer elements with at least three matching layers, at least one of which being formed into a tip covering the one or more transducer elements wherein the matching layer forming the tip is either low-density polyethylene (LDPE) or PEBAX, or some combination of both.

14. The method of claim 13, wherein the tip has a first body portion with first characteristics and a second body portion with second characteristics.

15. The method of claim 13, wherein the tip has an acoustic portion of desired thickness.

16. A method of making a probe tip comprising:

providing one or more transducer elements; and providing the one or more transducer elements with at least three matching layers, at least one of which being formed into a tip covering the one or more transducer elements, wherein the tip has a first body portion with first characteristics and a second body portion with second characteristics, wherein the first body portion forms a window and the second body portion forms a main body of the tip.

* * * * *